United States Patent [19]

Hayek

[11] Patent Number: 4,930,498

[45] Date of Patent: Jun. 5, 1990

[54] VENTILATOR APPARATUS AND FLUID CONTROL VALVE

[75] Inventor: Zamir Hayek, Herzlia, Israel

[73] Assignee: Dranez Anstalt, Vaduz, United Kingdom

[21] Appl. No.: 287,144

[22] Filed: Dec. 21, 1988

[30] Foreign Application Priority Data

Feb. 4, 1986 [GB] United Kingdom ............... 8602646
Jul. 26, 1986 [GB] United Kingdom ............... 8618254

[51] Int. Cl.⁵ ............................................. A61H 31/02
[52] U.S. Cl. ............................... 128/30.2; 128/205.26; 137/625.21; 137/625.46
[58] Field of Search ................ 128/30, 30.2, 202.12, 128/205.26; 604/21; 137/625.21, 625.46, 624.13

[56] References Cited

U.S. PATENT DOCUMENTS

| | | | |
|---|---|---|---|
| 924,382 | 6/1909 | Reynolds | 137/625.46 X |
| 1,084,410 | 11/1914 | Drennon | 137/625.46 X |
| 1,153,675 | 9/1915 | Coffin | 137/625.46 X |
| 2,089,943 | 8/1937 | Busby | 137/625.46 X |
| 2,223,570 | 12/1940 | McMillin . | |
| 3,096,787 | 7/1963 | Kayler | 137/625.46 X |
| 3,286,730 | 11/1916 | Beck | 137/625.21 X |
| 3,608,866 | 9/1971 | Karpacheva . | |
| 3,948,286 | 4/1976 | Dunbar et al. . | |
| 3,998,227 | 12/1976 | Holbrook et al. . | |
| 4,520,847 | 6/1985 | Baron . | |

FOREIGN PATENT DOCUMENTS 1056076 1/1967 United Kingdom .
2140133 11/1984 United Kingdom .

Primary Examiner—Alan Cohan
Attorney, Agent, or Firm—Cushman, Darby & Cushman

[57] ABSTRACT

A patient enclosure for ventilator apparatus comprising a base member (10) and a liftable cover member (12) which in an operative position defines a patient receiving chamber having at least one aperture (13) in the cover member for accommodating a portion of a patients body, the or each such aperture in the cover member being open along an edge of the cover member which overlies the base member in the operative position and containing a seal member for forming a substantially air tight seal in use between the cover member and the patients body and the base member, wherein the seal member takes the form of a flexible curtain (14) having a free edge overlying the base member and means such as straps (19) for tensioning a portion of the curtain to cause the curtain to seal against the base member and the patients body. The enclosure is used in conjunction with a source of oscillating air pressure to form a ventilator.

9 Claims, 9 Drawing Sheets

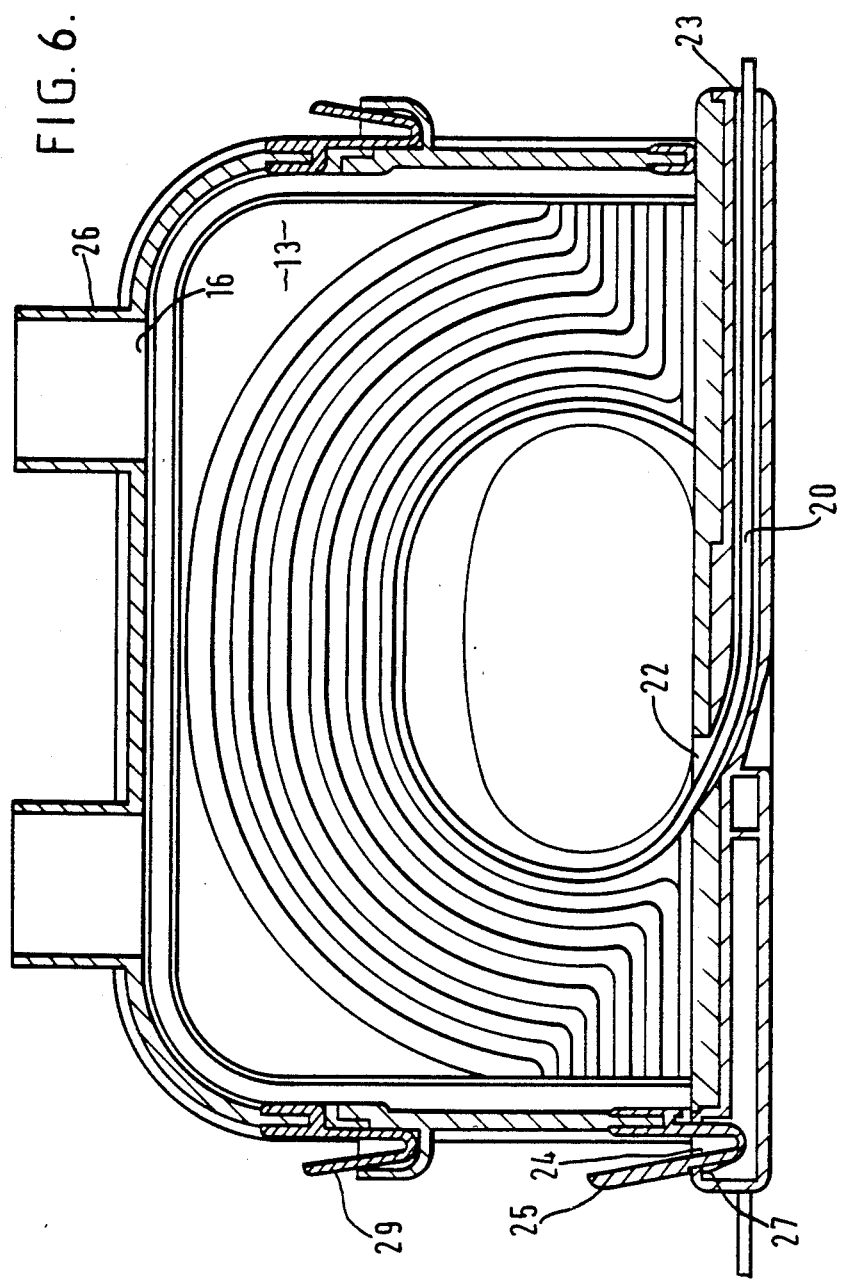

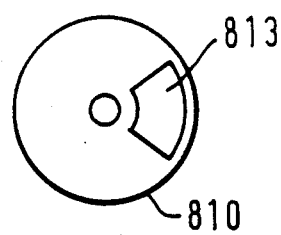
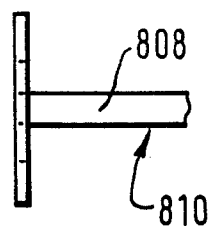
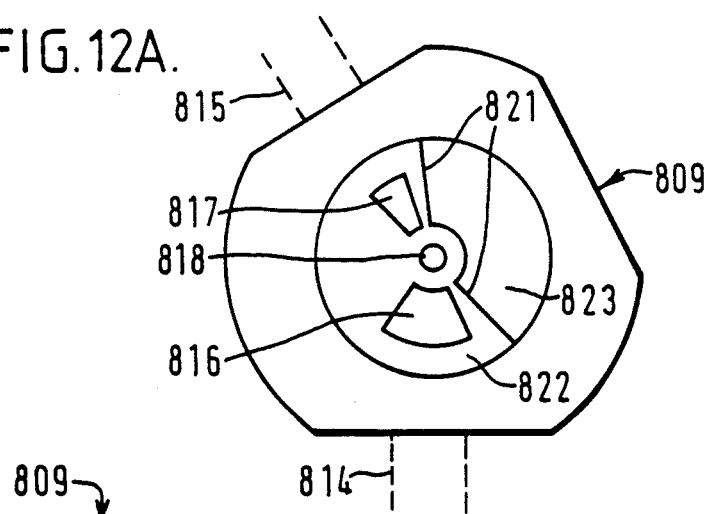
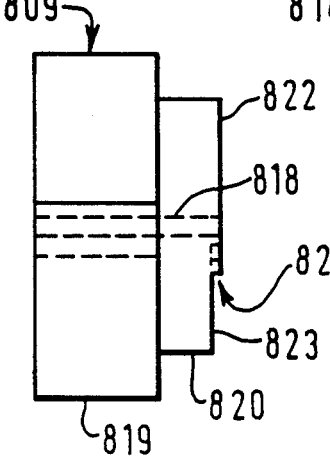

VENTILATOR APPARATUS AND FLUID CONTROL VALVE

This is a division of application Ser. No. 010,824, filed Feb. 4, 1987, now U.S. Pat. No. 4,815,452, issued 3/28/89.

The present invention relates, in one aspect, to patient enclosures for use in ventilator apparatus and to ventilator apparatus including such patient enclosures. In another aspect, the invention relates to fluid control valves, useful in particular, but not exclusively, for controlling air flow in such ventilator apparatus.

Many designs have been proposed in the past for apparatus for producing assisted or artificial respiration of patients. Apparatus under this general heading may be divided into two principal types. The first relies on intubation to allow the introduction of air through the trachea and into the lungs. The second method generally avoids intubation and relies on enclosing at least the chest region of the patient within an enclosure in which the air pressure is varied periodically to induce respiration.

The first aspect of the present invention relates to ventilators of this second type.

In ventilators of this type, the patient's head at least protrudes from the enclosure through a wall thereof and a seal must be made between the patient and the wall in order that pressure changes in the enclosure may be made. The present invention is in part concerned with the nature of such a seal.

Some means must be provided for allowing entry of the patient into the enclosure and the present invention is also concerned with this problem. In particular, as the patient is likely to be entirely dependant upon the use of the ventilator for respiration, the speed with which a patient may be placed in the ventilator and with which the ventilator may be put into operation is of great importance in many cases. If this procedure is not speedy and convenient it may be necessary to intubate the patient and use another type of ventilator temporarily. This is highly disadvantageous partly because intubation is a skilled procedure and partly because it carries with it significant risk of trauma.

These considerations are particularly important where the patient is an infant, particularly a neonate or preterm infant.

Previous ventilator enclosure designs have been unsatisfactory in respect both of the seals provided and the ease of access to the enclosure.

A form of seal widely employed in the past is described in U.S. specification No. 2863447. In general terms, this comprises a pair of mutually rotatable circular rim members surrounding the aperture through which the patient's body protrudes which rim members are spaced by a short distance longitudinally with respect to the patient's body. A soft flexible tube of plastics or rubber material is connected at one end to a first of the rim members and at the other to the second of the rim members. The rim members are mounted in a mutually rotatable manner. Rotation of the rim members with respect to one another produces folds and pleats in the soft tube which constrict the diameter of the tube and form a flexible and comfortable seal about the body of the patient.

As described in my European Patent application No. 86300413.1, I have found that it is advantageous to employ a ventilating pressure regime involving pressure oscillations in the enclosure of the ventilator about a negative base line pressure. I have found that it is difficult to obtain a satisfactory seal of the enclosure using a sealing mechanism as described above. Where a substantial negative pressure is to be maintained in the enclosure and a cyclic fluctuation of that pressure is to be imposed by an oscillator, a good seal of the enclosure is wanted. The application of too much pressure to the patient by the sealing members is undesirable as this can tend to affect venous blood flow and thus have a harmful effect upon the patient through undesirable changes in the blood circulation.

Using a sealing member of the kind described above, it is difficult to obtain a satisfactory seal without using too much pressure between the seal and the patient.

Finally, in preferred aspects of the invention there is provided an improved method of delivering of air to the enclosure which utilises the inward and outward flow of air to and from the enclosure as opposed to the pressure changes associated with that flow as a means of inducing respiration.

In a first aspect the present invention provides a patient enclosure for ventilator apparatus comprising a base member and a liftable cover member which in an operative position defines a patient receiving chamber having at least one aperture in the cover member for accommodating a portion of a patient's body, the or each such aperture in the cover member being open along an edge of the cover member which overlies the base member in the operative position and containing a seal member for forming a substantially airtight seal in use between the cover member and the patient's body and the base member, wherein the seal member takes the form of a flexible curtain having a free edge overlying the base member and means for tensioning a portion of the curtain to cause the curtain to seal against the base member and the patient's body.

Preferably, the cover member has a pair of said patient accommodating apertures, one at each of two opposite ends thereof. In apparatus of this kind, the head at least of the patient will extend out of one end of the enclosure and a part of the patient's lower body will protrude out of the other such aperture.

Preferably, the enclosure is so sized and the apertures are so sized and spaced as to be adapted to receive respectively the abdomen of an intended patient below the diaphragm and the upper chest in the region of the axilla.

A construction of this kind has particular benefits in respect of infant patients, particularly neonate or preterm infant patients. With such patients, there has previously been a difficulty in external ventilation using ventilators having an enclosure which receives the whole of the infant's body other than the head and which seals around the infant's neck. This difficulty is particularly encountered if a negative base line pressure is maintained in the enclosure. The negative pressure tends to suck the infant into the enclosure which places an excessive strain on the neck of the infant. Also, using seals of the kind previously proposed it has been difficult to obtain a satisfactory seal around the neck of a very young infant.

However, the improved seal provided by the present invention may be utilised in other forms of enclosure also including those intended for adult patients.

Preferably, the curtain is of rubber or plastics material. Preferably it is of pleated construction with the pleats forming ridges and valleys extending around the patient.

Preferably the means for tensioning a portion of the curtain at the or each aperture comprises a respective elongate, flexible tensioning member extending from each inner lower edge region of the curtain and passing below the upper surface of the base member in such a way as to draw the said lower edge region down on to the base member and toward the opposite side of the aperture.

Preferably the respective tensioning members are end regions of an integral elongate member extending around the inner edge of the curtain around the aperture and extending from inner lower corners of the curtain to provide the respective tensioning members.

Preferably each tensioning member is severable into inner and outer portions at a quick release in-line connector provided intermediate the length of the respective tensioning member.

Preferably each tensioning member is a strap.

Preferably each tensioning member is a friction fit within a portion of the base member through which the tensioning member passes, so as to maintain a desired tension in use.

With such an arrangement, after a patient has been placed in the enclosure, the or each seal may be brought into close engagement with the surface of the base member and the patient by pulling the tensioning members associated with the seal and the tension thereby imparted will be maintained by the frictional engagement of the tensioning member and the base member.

Preferably, each tensioning member extends through an aperture in the upper surface of the base member and runs beneath said upper surface to the edge of the base member opposite to the curtain edge associated with the tensioning member.

The use of a cover member incorporating a patient receiving aperture open along the edge overlying the base member enables the placing of a patient in the ventilator apparatus by lying the patient on the base member and bringing the cover member down over the patient so that the open sided aperture or apertures of the cover member fit over the patient and are then sealed.

To this end, the cover member may be detachable from the base member along all four sides or may be hinged to the base member on one longitudinally running side.

Preferably, quick release catches are provided for securing the base member and the cover member together.

Preferably, the cover member has at least one port for connection to an oscillator for inlet and outlet of gas or pressurising and depressurising the chamber relative to a base line pressure.

Preferably, a pair of said ports are provided on either side of the longitudinal mid-line of the chamber.

Preferably, such ports are positioned to overly upper chest regions of a patient in the enclosure.

As will be explained in more detail hereafter, it is particularly preferred that in use such an enclosure is used in connection with an oscillator capable of blowing air into the chamber through the two ports and withdrawing air from the chamber through the two ports at a velocity such as to establish flows of air moving within the chamber of sufficient velocity to urge movement of the chest wall of the patient.

A portion of the cover member may form a removable hatch to provide access to a patient without disturbing the seal between the enclosure and the patient.

The invention includes ventilator apparatus for use in providing assisted or artificial respiration comprising an enclosure as described above according to the first aspect of the invention and an oscillator unit adapted to supply air to and withdraw air from the enclosure to vary the pressure therein periodically.

It is particularly preferred that the oscillator be generally as described in my co-pending European Patent Application No. 86300413.1.

In particular, it is preferred that the oscillator include means for establishing a sub-ambient pressure in the enclosure and means for varying the pressure in the enclosure so as to superimpose on the sub-ambient pressure a cyclic variation, preferably having a frequency of above 1 Hz.

Preferably, the means for establishing a sub-ambient pressure in said enclosure is adapted to produce a negative base line pressure of at least 196 Pa (2 cm $H_2O$), e.g. from 196 Pa to 2940 Pa (30 cm $H_2O$) more preferably from 196 Pa (2 cm $H_2O$) to 1961 Pa (20 cm $H_2O$).

Preferably, the means for establishing a sub-ambient pressure in said enclosure is adjustable to provide a desired sub-ambient pressure and as the most preferred mean enclosure pressure is about $-980$ Pa ($-10$ cm $H_2O$), preferably at least a range of from $-490$ Pa (5 cm $H_2O$) to $-1470$ Pa (15 cm $H_2O$) is available.

Preferably, the means for varying the pressure in the enclosure is adapted to produce a pressure variation amplitude of from 392 Pa (4 cm $H_2O$) to 3136 Pa (32 cm $H_2O$).

Preferably, the means for varying the pressure in the enclosure is adjustable to produce a desired amplitude of pressure variation such as from 785 Pa (8 cm $H_2O$) to 1570 Pa (16 cm $H_2O$).

Preferably, the means for varying the pressure in the enclosure is adjustable to provide a desired shape of waveform for said cyclic pressure variation. It may for instance be possible to vary the I/E ratio, to choose between two or more of a sine wave pattern, a square wave pattern or a saw tooth wave pattern for the whole of the pressure variation, or for parts of the wave form or to choose other wave forms.

It may be convenient for said means for establishing a sub-ambient pressure in said enclosure, and means for varying the pressure in said enclosure so as to superimpose on said sub-ambient pressure a cyclic variation having a frequency of above 1 Hz to be provided in combination by a pump unit.

Where there is access to a source of vacuum and a source of pressurised air the pressure variations are conveniently provided by using a fluid control valve having an output connected to the enclosure, a first input connected to a source of air under pressure, and a second input connected to a source of sub-atmosphere pressure (a vacuum source), the control valve connecting the output alternatively to the source of pressurised air and to the vacuum source. The source of pressurised gas may be, for example a pressurised air line in a hospital ward, or a locally-provided air compressor. Where a vacuum suction line is provided, for example adjacent the pressurised air source, the vacuum for the vacuum enclosure may be provided by connection to the suction line. Alternatively, the vacuum source may be a vacuum pump, which pump may be driven by the source of air under pressure.

The fluid control valve preferably embodies a third aspect of the invention, described below.

Alternatively, the pressure may be varied by means of a pump unit. According to a second aspect of the invention, a pump unit comprises a piston member for driving a volume of air cyclicly into and out of said enclosure to produce said pressure variation, and valve means positioned and adapted to vent a proportion of the air displaced by said piston member out of the ventilator to establish said sub-ambient pressure in the enclosure.

Said piston member may be a flexible diaphragm secured around an edge region thereof to close a pump chamber and having a central region which is reciprocable to pump air to and from pump chamber, said pump chamber communicating with said enclosure.

Said valve means may be a non-return valve allowing limited air flow out of said enclosure.

Preferably, said means for varying the pressure in said enclosure comprises a motor operating a pump unit, which motor is a variable speed motor.

Preferably, said variable speed motor is a stepping motor. By feeding suitable patterns of stepping pulses to the motor, any desired waveform of pressure variation may then be obtained and both shape and frequency of the waveform may be varied at will.

Preferably, said piston member is reciprocable along a first axis, a motor is provided having an output shaft rotating about a second axis parallel to the first axis, a radius member is provided extending radially of the output shaft and connected to rotate therewith about the first axis, and a link is provided between the piston member and the radius member.

Suitably, the means for varying the pressure in the chamber is adapted to produce cyclic variations in said pressure at a frequency of from 3 to 12 Hz.

The frequencies most advantageously used are from 4 to 8 Hz, e.g. about 5 Hz.

The present invention also includes a method of assisted ventilation of a patient comprising placing at least the trunk of a patient within the enclosure of a ventilator as described herein, and applying said cyclic pressure changes to the said enclosure to assist respiration.

According to a third main aspect of the invention, there is provided a valve for controlling fluid flow between a common flow path and two alternative flow paths, which comprises a main port communicating with a main chamber, at least two subsidiary ports each communicating with a respective subsidiary chamber, said subsidiary chambers being mutually isolated and separately connectable to the main chamber, a rotary shutter member which controls fluid flow between the main and subsidiary chambers, and a motor for selectively rotating the shutter member, the shutter member having a shutter opening so disposed in relation to the said chambers that the shutter member is rotatable between a range of positions for each subsidiary chamber at which fluid flow is permitted through the shutter opening only between that subsidiary chamber and the main chamber, and through a range of positions in which the subsidiary chambers are all mutually isolated, wherein said subsidiary chambers open to the main chamber at respective openings in a face of a valve seat, e.g. lying in substantially a common plane, and said shutter member has a sealing face overlying said openings. Preferably, there are two (first and second) subsidiary ports and respective chambers.

Such a valve may be used, for example, to provide alternately low and high pressures to a ventilator connected to the main port, first and second subsidiary ports being connected respectively to a source of pressurised air and of vacuum. Isolation of the subsidiary chambers from one another prevents air flow from the source of pressurised air to the vacuum source. The rate of flow between the main port and each subsidiary port preferably varies with the position of the shutter opening within the range of positions for that subsidiary port. This enables the fluid flow to be controlled cyclically in accordance with any desired flow sequence. For example to vary the I/E ratio, to choose between two or more of a sine wave pattern, a square wave pattern or a saw tooth pattern, for the whole of the pressure variation, or for parts of the wave form or to choose other wave forms.

The shutter member preferably consists of a plate, the shutter opening being an aperture therein. Preferably, the plate is a disc, the aperture being off-set from the centre of the disc, and the selector member further comprising a spindle connected to the disc for controlled rotation of the aperture about an axis.

The first and second subsidiary chambers are preferably spaced, e.g. parallel, bores in a body portion of the valve, whose respective ends lie in said common plane sealing against the disc. The said bores are preferably shaped as spaced sectors of an annulus, when viewed in cross section, the arrangement being such that the disc aperture overlaps successive sector-shaped ends of the bores as the disc is rotated. The minimum cross-section of the first subsidiary chamber is preferably substantially larger than that of the second subsidiary chamber. The valve is then capable of compensating for differences in the fluid pressures applied to the first and second subsidiary ports. The control valve comprises a motor connected to drive the shutter member between its said first, second and third ranges of positions. The motor is preferably an electronic stepper motor. Preferably, the motor is controlled by an electronic processor in accordance with a predetermined program whereby the first and second subsidiary chambers are periodically and alternately connected to the main chamber.

More generally, the invention includes apparatus comprising a patient enclosure as described above having a port for inward and outward flow of air connected to the main port of a control valve, which valve comprises said main port communicating with a main chamber, first and second subsidiary ports communicating with first and second mutually isolated subsidiary chambers separately connectable to the main chamber and a movable shutter having a shutter aperture positionable selectively to connect for gas flow each separately of the first and second subsidiary chambers to the main chamber or to isolate the main chamber from both subsidiary chambers.

Preferably, accumulator reservoirs are connected to either or to each of said first and second subsidiary ports, the or each accumulator reservoir being for connection to a source of gas pressure or vacuum.

Preferably, the apparatus includes a pressure sensor for sensing gas pressure at or adjacent said main port or in said ventilator enclosure.

Preferably, the apparatus includes electronic circuitry for controlling the movement of said shutter member to provide a desired pattern of pressure changes at or adjacent said main port or in said ventilator. Preferably, said circuitry makes use of signals from said pressure sensor to control said shutter member.

The invention will be further illustrated by the following description of specific embodiments with reference to the accompanying drawings in which:

FIG. 6 is a section corresponding to FIG. 4 through a second embodiment according to the invention including a modified seal arrangement;

FIG. 11A is a view of a shutter disc of the fluid control valve of FIG. 9, taken along the axis of the valve from the input end thereof;

FIG. 11B is a side elevation of the shutter disc of FIG. 11A;

FIG. 12A is an elevation of the valve body of the fluid control valve of FIG. 9, taken along the axis from the output end thereof; and FIG. 12B is a side elevation of the valve body of FIG. 12A.

Figure 1:
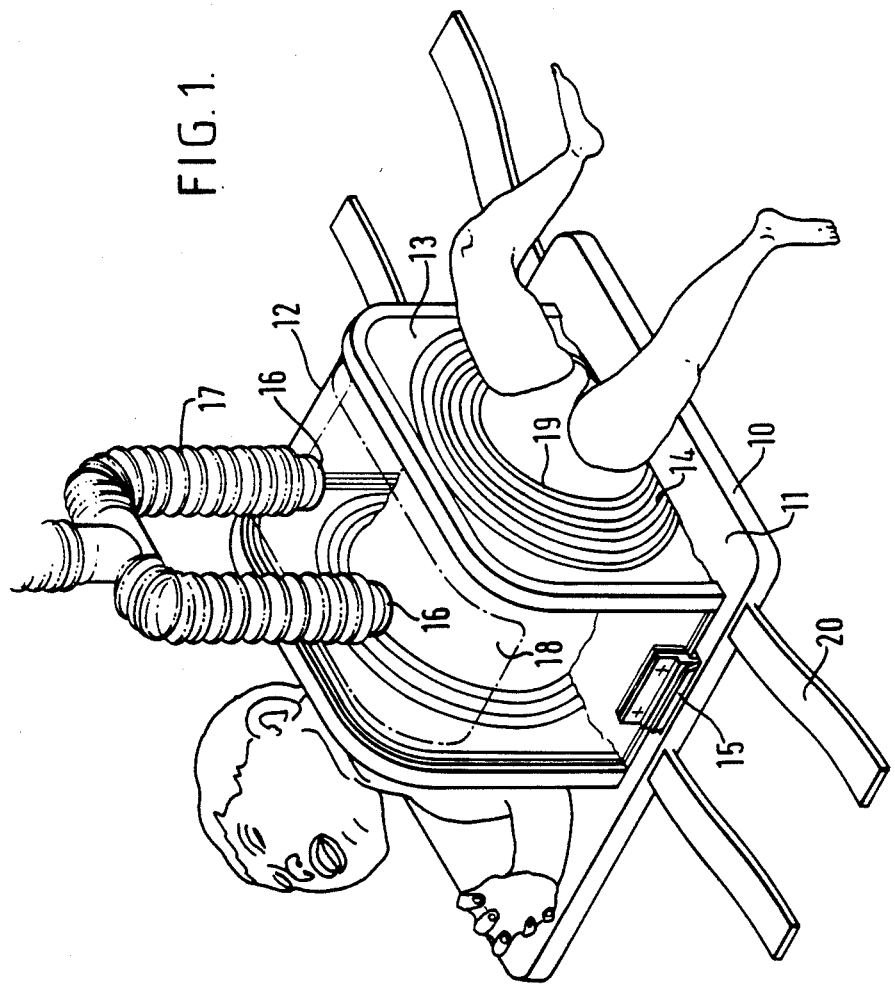
FIG. 1 is a perspective view of a patient enclosure of ventilator apparatus according to the first aspect of the invention in use.

As shown in FIG. 1, a ventilator enclosure according to the invention includes a base member 10 providing a patient receiving upper surface 11 upon which is shown an infant patient being provided with artificial respiration by the ventilator.

The ventilator further comprises a cover member 12 of a generally flattened U-shape defining a tunnel over the trunk of the patient. The cover member comprises open ends providing apertures 13 through which pass the body of the patient. Each aperture 13 is provided with a sealing member 14 in the form of a pleated rubber curtain attached along all three sides of the end of the cover member 12.

The cover member is detachable from the base by releasing quick release latches 15 positioned one on each longitudinally running edge of the cover member.

A pair of air inlet/outlet ports 16 are provided lying one either side of the longitudinal mid-line of the cover member and above an upper chest region of the patient. The ports 16 are connected to an oscillator for producing pressure changes in the enclosure via flexible tubes 17 meeting at a T-junction before being connected to the oscillator.

The ports 16 are provided in a detachable hatch portion 18 of the cover member which is removable to provide access to the chest of the patient.

Figure 2:
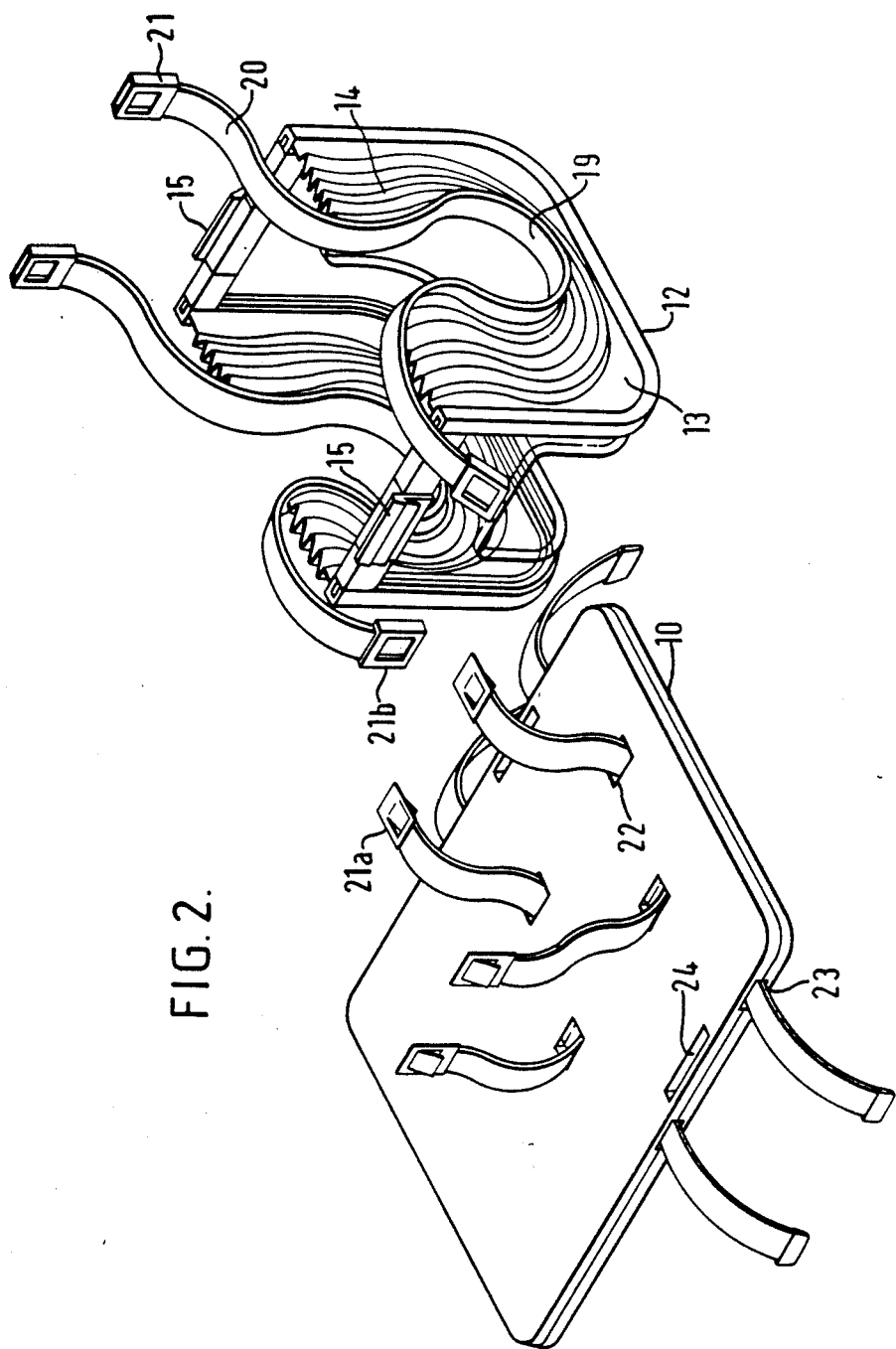
FIG. 2 is a perspective view of the ventilator enclosure of FIG. 1 with the cover member shown separated from the base member and inverted.

As shown in FIG. 2, the cover member is seen detached from the base member and the structure of the curtain 14 can be better seen. Each end of the cover member defines a generally U-shaped aperture 13 with the open end of the U bordering the connection between the cover member and the base member. The sealing curtain 14 is pleated so that the ridges and valleys provided by the pleats extend generally circumferentially of the patient received in the aperture. Around the inner edge of the curtain there is provided a strap member 19 which is integral with the curtain 14 and extends around the inner edge thereof between lower inner corner portions of the curtain. From the corner portions, the strap 19 extends on each side as a tensioning member 20. Each tensioning member 20 is provided with a quick release in-line coupling 21 intermediate its ends comprising male and female members 21a, 21b. Thereafter each tensioning member 20 extends through a respective aperture 22 in the surface of the base member and runs beneath the upper surface of the base member and exits through a respective rectangular aperture 23 in a side wall of the base member. It will be seen that each tensioning member 20 exits through a respective aperture 23 in that longitudinally running side of the base member which lies opposite to the side of the aperture from which the tensioning member originated.

Figure 4:
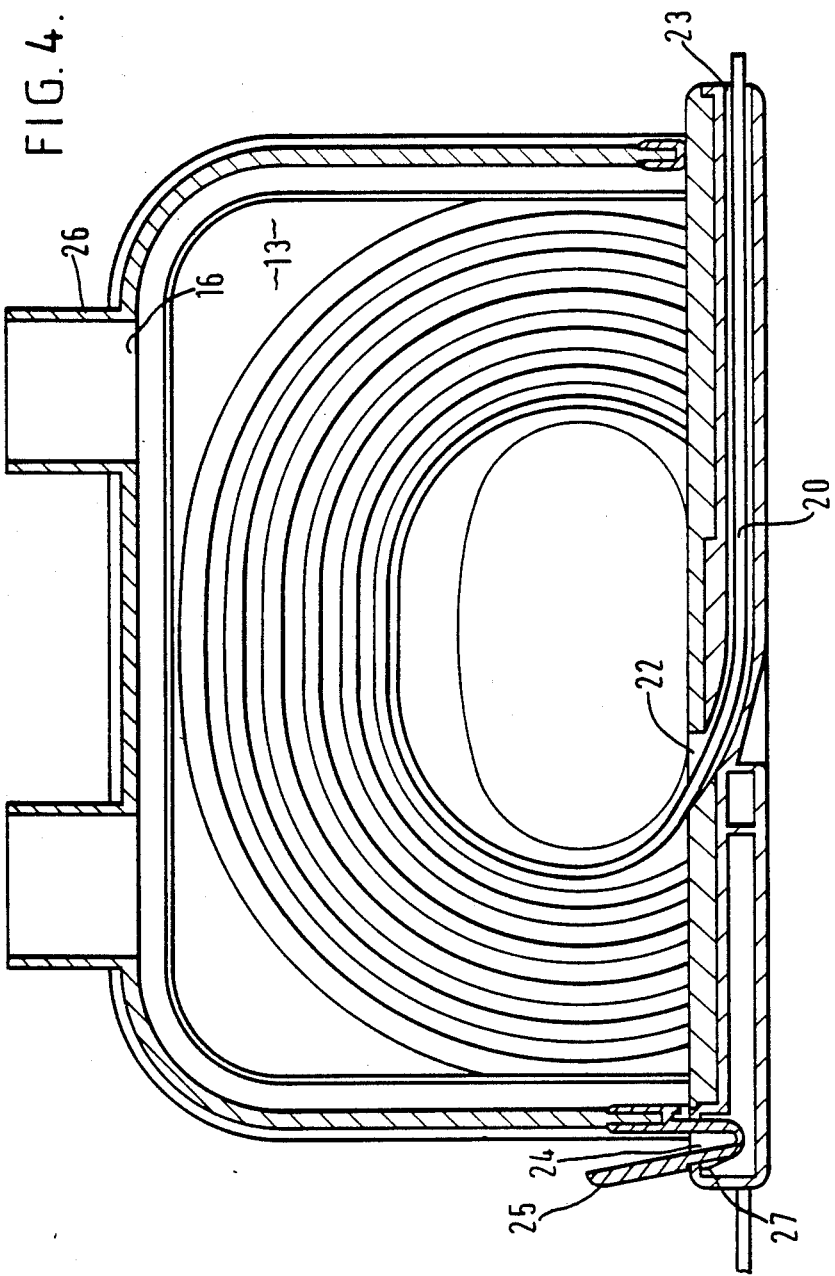
FIG. 4 is a section on the line A-A of FIG. 3.

This is more clearly seen by reference to FIG. 4 in which the course taken by the tensioning member 20 through the aperture 22 in the base member upper surface and beneath the base member upper surface to the side outlet 23 is clearly seen.

Also clearly seen in FIG. 4 is the pattern of pleating of the curtain 14.

As is also best seen in FIG. 4, the quick release latches 15 comprise an upwardly facing slot 24 in the base member immediately outside the line taken by the longitudinally running edge of the cover member cooperating with a catch member 25 provided on the cover member. The catch member 25 is generally U-shaped in cross-section with the bight of the U pointing downwardly so as to be able to enter the slot 24. A catch formation 27 including an upwardly facing abutment is provided on the exterior surface of the catch member 25 and catches beneath the wall bounding the exterior side of the aperture 24 but is displaceable inwardly by pressure on the catch member 25 to release the latch.

Figure 3:
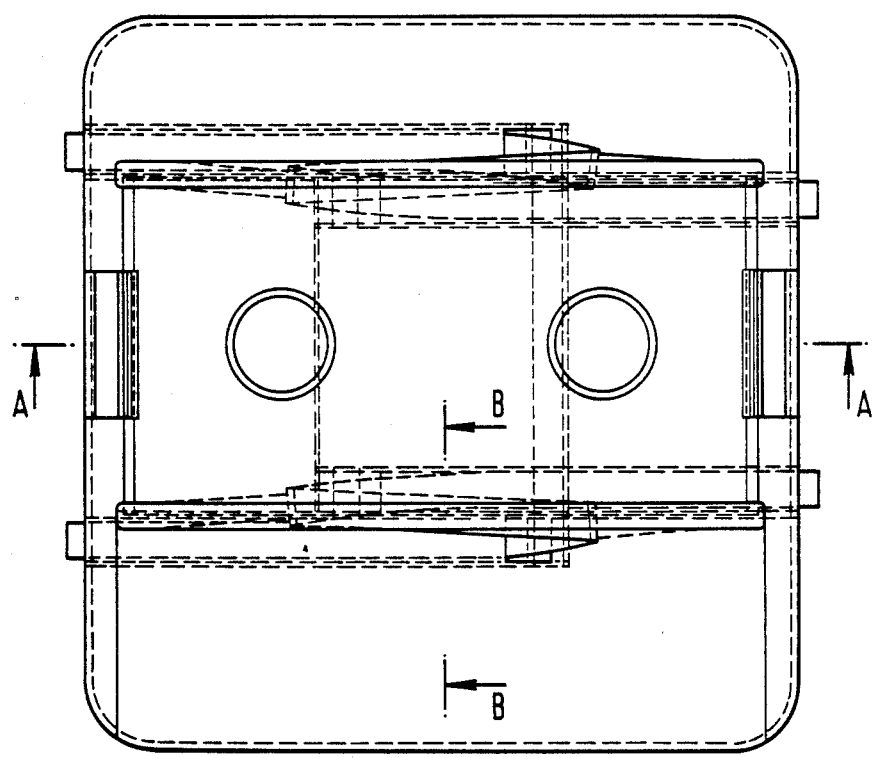
FIG. 3 is a plan view of the ventilator enclosure of FIG. 1.

Also clearly seen in FIG. 4 are the ports 16 each of which is provided with an upstanding tubular connector portion 26 for receiving a connecting hose 17. As seen in FIG. 3, each port 16 is situated on the transverse mid-line of the cover portion equally spaced about longitudinal mid-line and hence directly over the upper chest region of an infant in the chamber.

Figure 5:
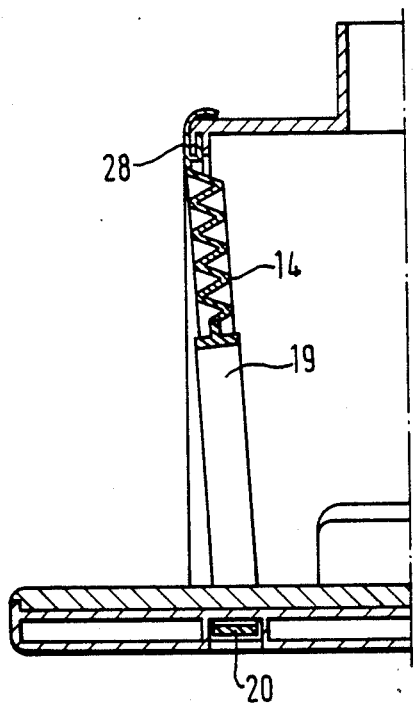
FIG. 5 is a section on the line B-B of FIG. 3.

As best seen in FIG. 5, the curtain 14 is integral with the strap 19 on its inner edges and with a sealing formation 28 on its outer edge by means of which the curtain is attached around the inner periphery of the aperture in the end wall 13.

The base member is hollow and is provided with bulk heads defining channels in which run the tensioning straps 20 as is also clearly seen in FIG. 5.

The tensioning straps 20 are made close fit with at least a portion of the channels in which they run in the base member so that they will remain in any position to which they are set.

In use, the cover member is first detached from the base member by releasing the catches 15, pulling on the straps 20 to loosen them and uncoupling the in-line quick release connectors 21. An infant patient is laid on the upper surface of the base member 10, the connectors 21 are reconnected and the tensioning straps 20 are pulled to bring the cover member generally down into position until the catch members 25 of the latches 15 snap home in the slots 24 and to draw the curtains 14 to seal both against the patient along the line of the strap 19 and also to seal against the base member along the free pleated lower edges of the curtains.

It has been found that this operation can be carried out at least as quickly as can intubation by a skilled practitioner. Whilst intubation is an extremely skilled procedure, the assembly over a patient of the enclosure described above is straightforward and requires only a little practice to be performed quickly and reliably.

Previous designs of ventilator enclosure for a directly comparable purpose have involved passing the patient through apertures into the enclosure and this has proved to be much more time consuming than the use of the apparatus specifically described above. It is to be appreciated that in the use of such a ventilator apparatus, the saving of seconds in introducing a patient into the enclosure is of importance.

A slightly modified enclosure according to the invention is shown in FIG. 6. The enclosure shown in FIG. 6 differs from that described previously in the formation of the pleats of the curtain. Instead of these running down onto the free edge of the curtain to produce a zig-zag pattern at the lower edge, in the embodiment shown in FIG. 6 the pleats each turn to run parallel to the base to the side edge of the aperture 13. Accordingly, along the lower edge of the aperture adjoining the base member the curtain presents a straight sealing edge instead of a zig-zag one.

FIG. 6 shows in detail quick release latches 29 securing in position the panel 18 containing the apertures 16.

The enclosure illustrated is preferably employed in combination with an oscillating pressure source which may comprise a source of constant negative pressure connected to gas connections 16 of the enclosure whereby a background negative pressure is established in the enclosure at a desired level together with a source of oscillating pressure such as a piston pump adapted to pump a constant volume of gas backwards and forwards into and out of the enclosure connected through the same connection 16 of the enclosure.

Preferably, both the source of constant negative pressure and the oscillating pressure source are adjustable so that the mean enclosure pressure, the span of the pressure variation about the mean and the frequency are all selectable by the user.

Figure 7:
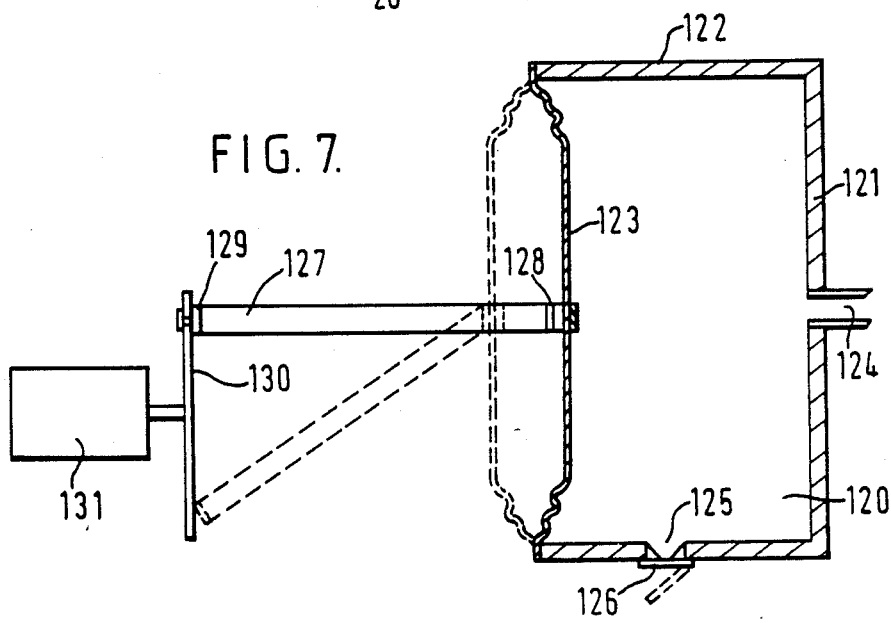
FIG. 7 is a section through an oscillator unit for use in conjunction with the enclosures of FIGS. 1 and 6.

An alternative form of oscillating pressure source is shown in FIG. 7. This is adapted to produce through a single connection both a negative mean enclosure pressure and the required oscillation of the pressure.

The oscillating pressure source shown in FIG. 7 comprises a pump unit comprising a pressure chamber 120 having a front wall 121 and an annular side wall 122 with a flexible diaphragm 123 closing the rear of the pressure chamber to define a generally cylindrical volume within the pressure chamber which is variable by axial displacement of the diaphragm 123. A gas outlet 124 is provided in the front wall 121 for connection to the enclosure.

A valve port 125 is formed in the annular wall 122 and is covered by a valve flap 126 hinged for outward movement to the position shown dotted. Valve flap 126 is resiliently biassed to the closed position by means not shown. Suitably, the biassing of flap 126 is simply by virtue of its own natural resilience.

A link shaft 127 is connected to the centre of diaphragm 123 by a universal joint 128. At its other end, link shaft 127 is connected through a universal joint 129 to an eccentric position on a disc 130 which is mounted for rotation by a stepping motor 131 at its axis. Disc 130 serves as a radius member mounting one end of link 127 for rotation eccentrically about the axis of the motor 131.

As shown in the figure, the diaphragm 123 is axially displaceable by rotation of the disc 130 by the motor 131. The position adopted by the diaphragm and the link 127 at an opposite extreme part of the rotational cycle is shown by dotted lines in the figure.

Rotation of the motor 131 produces reciprocating movement of the diaphragm 123 acting as a piston member to displace gas backwards and forwards through the connection 124.

As the diaphragm 123 moves to compress in the pressure chamber 120 and to displace gas out of the connection 124, the valve flap 126 opens and some gas is lost from the pressure chamber 120 through the valve port 125. Valve flap 126 closes to prevent reentry of gas from the exterior when the diaphragm 123 is withdrawn by the motor 131. Thus, although gas is pumped to and from through connection 124, some gas is continuously lost from the system generating a negative base line pressure. Of course, gas also enters the enclosure through any leak present in the seals so mitigating the negative pressure produced by the action of the valve 125, 126.

The motor 131 is a stepping motor and is driven by the provision of suitable stepping pulses. These may be produced by suitable microprocessor circuitry and sequencies of pulses may be sent to the motor to produce any desired variation in speed within a single revolution. Thus, the pressure wave form produced at the connection 124 may be closely controlled by the provision of suitable control circuitry and the user may be provided with the means to shape the wave form as he desires as well as to choose the frequency of the pressure oscillation, the mean enclosure pressure and the span of the pressure changes.

Figure 8:
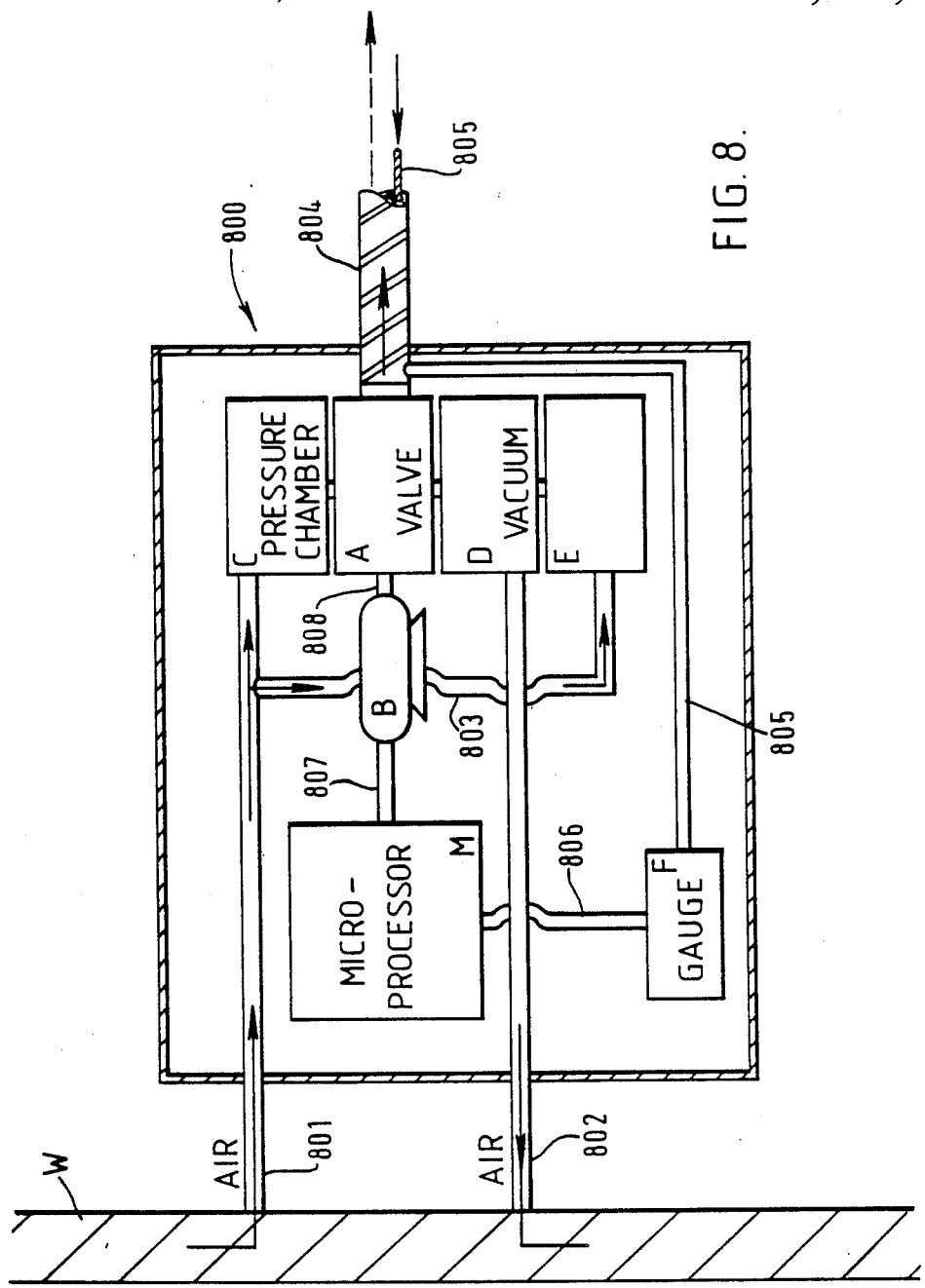
FIG. 8 is a schematic diagram of a pressure oscillator incorporating a fluid control valve in accordance with the third aspect of the present invention.

A further alternative form of oscillating pressure source is that pressure oscillator shown in FIG. 8. This pressure oscillator is capable of producing oscillations in the pressure within the ventilator, and can be arranged to provide a negative mean enclosure pressure.

The pressure oscillator 800 comprises a fluid control valve A whose output is connected to the ventilator enclosure by way of an output pipe 804. The valve A has two alternative inputs, connected respectively to a pressure chamber C and a vacuum enclosure D. The valve A is controlled by means of an electronic stepper motor B to connect the output either to the pressure chamber C or to the vacuum enclosure D.

The pressure chamber C receives pressurised air through an air pipe 801, for example from a source located in the wall W of a hospital. The vacuum enclosure D may be connected, through an air pipe 802, to a suction pipe, for example in the hospital wall W. However is such a suction pipe is not available, the vacuum in the vacuum enclosure D can alternatively be provided by means of a vacuum pump E connected thereto, the vacuum pump E being driven by means of pressurised air conveyed to the vacuum pump E by way of a further air pipe 803 which is connected to the source of pressurised air.

The electronic stepper motor B is controlled by a microprocessor M through a control line 807. The microprocessor M monitors the output air pressure, i.e. the pressure in the ventilator enclosure, by means of a pressure gauge F whose input is connected by way of a pressure line 805 to the interior of the ventilator enclosure, and whose output is connected by way of control line 806 to the microprocessor M. The pressure line 805 conveniently passes through the output air pipe 804 which links the fluid control valve A and the ventilator enclosure.

The fluid control valve A will now be described in greater detail with reference to FIGS. 9 to 12B. The valve A comprises a valve body 809, an output port 812a leading to an output chamber 812 in screw-threaded engagement with the valve body 809, a pressure port 815 at one side of the valve body, a vacuum port 814 at the opposite side of the valve body, and a shutter disc 810 retained by a bearing disk 811 and drivingly connected by a spindle 808 to the stepper motor B. The "output port" and "output chamber" will be so referred to for convenience but it will be apparent that the flow of gas therethrough is in fact oscillating and not solely or predominantly in the outward direction. The valve body 809 and output chamber 812 are coaxial, and the valve body 809 has an axial bore which receives the spindle 808 of the shutter disc 810.

As shown in FIGS. 11A and 11B, the shutter disc 810 consists of a circular disc from which depends axially the spindle 808. A shutter aperture 813 is formed in the disc off the centre thereof. The shutter aperture 813 subtends an angle of approximately 70°, and has the shape of a sector of an annulus.

Figure 9:
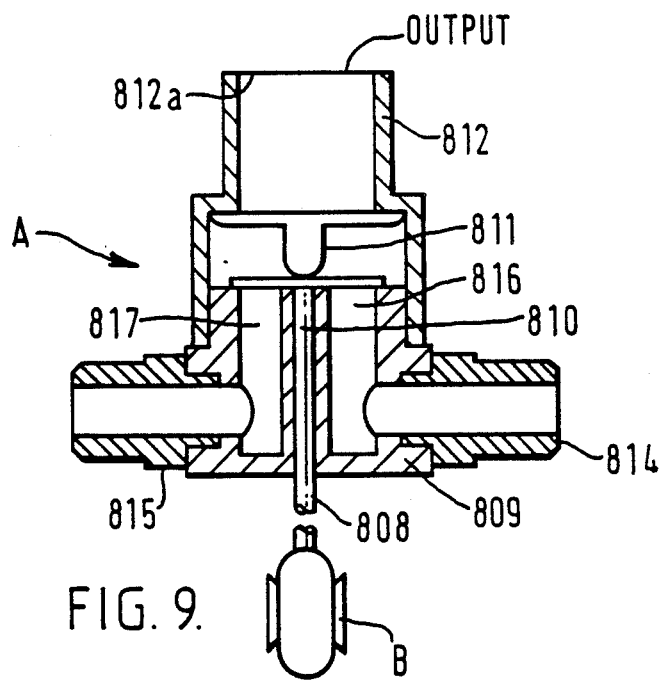
FIG. 9 is a schematic axial section through the fluid control valve of FIG. 8.
Figure 10A:
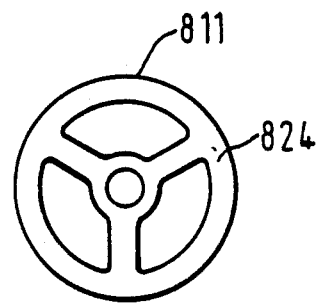
FIG. 10A is a view from the output end of a bearing disc incorporated in the fluid control valve of FIG. 9.
Figure 10B:
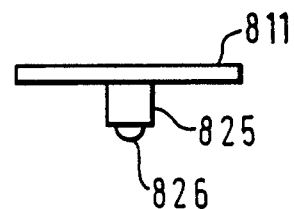
FIG. 10B is a side elevation of the bearing disc of FIG. 10A.

As shown in FIGS. 10A in 10B, the bearing disc 811 consists of a circular disc 824 from which depends axially a short bearing shaft 825 on whose end is mounted a ball bearing 826. The disc 824 is formed with three large apertures, shaped as sectors of an annulus, to enable air to flow through the bearing disc 811. As shown in FIG. 9, the bearing disc 811 is mounted coaxially within the output chamber 812. The upper peripheral surface of the disc 824 abuts against an annular shoulder between two sections of the output chamber of different internal diameters. The ball bearing 826 engages the centre of the upper surface of the shutter disc 810, ensuring that the shutter disc remains in its seating within the valve body 809, but allowing the shutter disc to rotate.

As shown in FIGS. 9 and 12A, the valve body 809 has a pressure input chamber 817 and a vacuum input chamber 816, these chambers being mutually isolated and communicating respectively with the pressure input and vacuum input ports 815, 814. The input chambers 816, 817 are formed as paraxial bores in the valve body 809, each having the shape of a sector of an annulus, when viewed in cross-section. The lower end of each input chamber is closed, while the upper ends, at the interface with the shutter disc 810, lie in a plane which is common to the disc of the shutter disc 810.

The pressure input and vacuum input chambers 817, 816 are arranged relative to the shutter disc 810 such that the shutter aperture 813 registers with either or neither of the input chambers but never with both of them at the same time. As the shutter disc 810 rotates, it assumes either a first range of positions, at which air flow is permitted only through the shutter opening between the pressure input chamber and the output chamber and at a variable rate dependant on a precise position within the first range, a second range at which flow is permitted only between the vacuum input chamber and the output at a variable rate dependent on the precise position within the second range, and a third range at which the input and output chambers are all mutually isolated.

The cross-sectional area of the vacuum input chamber 816 is approximately twice the cross-sectional area of the pressure input chamber 817. This is to provide an extra constriction in the flow of pressurised air to the output chamber, to compensate for the fact that there is a greater pressure difference between the pressure chamber C and the mean output pressure than between the vacuum enclosure D and the mean output pressure.

As shown in FIGS. 12A and 12B, the valve body 809 has a base portion 819, shaped as an irregular triangle with rounded vertices, from which depends from its centre an externally-threaded, cylindrical portion 820, for screw-threaded engagement with the output chamber 812. A shallow lip is cut into the upper surface of the cylindrical portion 820 of the valve body, at the interface with the shutter disc 810. The ledge 823 subtends an angle of approximately 140°, and is divided from the remainder 822 of the upper surface of the cylindrical portion 820 by a ridge 821. The purpose of the ledge 823 is to reduce friction between the undersurface of the shutter disc 810 and the adjacent upper surface of the cylindrical portion 820 of the body member, against which the shutter disc slides in use.

The cyclic pressure oscillations applied to the ventilator enclosure are produced as follows.

The values of the maximum and minimum pressures are determined by selecting the precise angular position of the shutter disc 810, so that the required proportion of the total area of the relevant input chamber 816 or 817 is opened by the shutter 813. This is achieved by the electronic stepping motor B, controlled by the microprocessor M. Further, the variation of pressure with time is controlled by precise timing of the movement of the shutter disc 810. For example, the shutter opening 813 could be moved rapidly or more slowly over the appropriate input chamber, and the dwell time could be a small or a large proportion of the overall cycle.

The electronic stepping motor B is preferably capable of moving the shutter disc back and forth in a reciprocating motion alternately over the two input chambers, at a frequency of from 1 to 1800 times per minute, thus causing air pressure oscillations at a corresponding frequency. The wave shape of the pressure oscillations can be controlled as required, for example to a saw tooth, square or sine wave.

It has been found that the regime of pressure changes and mean enclosure pressure described above enable the ventilation of patients whose lungs are not healthy, for instance neonates with IRDS, whereas previous proposals for external high frequency ventilation have proved effective only for brief periods in animals with healthy lungs in laboratory tests.

Moreover, it has been found that the pumping of air into the enclosure through apertures 16 positioned directly over the chest, as opposed to simply opening a connection between the enclosure and atmosphere or locating the apertures in the sides of the enclosure, has important consequences.

The jet of air into the chamber impinging upon the chest wall serves to start downward movement of the chest wall before the resulting increase of pressure in the enclosure as a whole takes effect. The suction produced by the outflow of air at the commencement of the falling-pressure phase of the cycles serves to start chest inflation before the resulting drop in pressure in the enclosure as a whole would do so.

Thus, the coupling between the air flow to and from the chamber and chest wall movement can be much improved by disposing the air inlet/outlet ports so as to produce these local pressure effects.

To this end, the pump or pressure oscillator is preferably capable of delivering through the connection to the enclosure an air flow of at least twice the velocity that would be obtained by connecting the inlet port to atmosphere through an equivalent flow path, preferably 3 or more times the velocity.

Compared to existing methods and apparatus for assisted ventilation the apparatus described above has substantial advantages. Intubation is avoided and with it all of the associated complications.

As compared to negative pressure ventilators of prior designs, the ventilator described with reference to the drawing is of low cost since it does not seek to replace the incubator and allows the use of a conventional incubator.

The head, shoulders and arms and the lower part of the patients body are left accessible for routine or emergency procedures. There is therefore no need to interfere with the process of ventilation to keep the infant clean and dry or to install or maintain drips or other lines.

Because it can be arranged that the air moving in and out of the ventilator is drawn from the incubator, the temperature of the infant can be controlled satisfactorily and this is made even easier by the fact that a substantial part of the patients body is not involved in the ventilator but is simply in the atmosphere of the incubator.

Because there are two opposed diaphragms there is little or no tendency for the negative pressure to seek to draw the patient further into the enclosure of the ventilator. Strain on the neck of very small babies is avoided as the seal of the ventilator is made around the axilla. However, even if one were to choose to make the upper seal around the patients neck, there would be little or no strain imposed on the neck by the operation of the ventilator because of the use of two diaphragms.

Accordingly, babies may be ventilated using such a ventilator irrespective of their weight.

Whilst the invention has been described with particular reference to infant patients, methods and apparatus of the invention constructed on a suitable scale may be employed with adult patients also.

Whilst the invention has been described with reference to specific characteristics of the embodiment described, many modifications and variations thereof are possible within the scope of the invention.

For example, while the third aspect of the invention has been illustrated with reference to the embodiment shown in FIGS. 8 to 12B, it is envisaged that the fluid control valve could take other forms. The cross-sectional areas of the two input chambers 816, 817, for example, could be of any relative size, and these chambers could be formed at any circumferentially-spaced positions in the valve body. Further, the valve could be provided with three or more inputs, with corresponding separate input chambers, each of which may be brought separately into communication with the output chamber.

I claim:

1. Ventilator apparatus for use in ventilation of the lungs of a patient, comprising a ventilator enclosure for receiving at least the chest region of the patient's body, and means for varying the pressure in the enclosure to produce ventilation, said pressure varying means comprising a source of positive gas pressure, a source of negative gas pressure, and valve means connected between said sources and said housing, said valve means comprising a valve body, a main chamber and at least two subsidiary chambers in said valve body, a main port connected for gas flow to said housing and communicating with the main chamber in said valve body, at least two subsidiary ports, one subsidiary port being connected for gas flow to said source of positive pressure and the other said port being connected for gas flow to said source of negative pressure and each said port communicating with a respective said subsidiary chamber in said valve body, a valve seat in said valve body, said subsidiary chambers being mutually isolated and opening into the main chamber at respective openings in said valve seat, a rotary shutter member having a sealing face overlying said valve seat openings which controls fluid flow between said main and subsidiary chambers, and an electronic stepper motor connected to said shutter member for selectively rotating the shutter member, the shutter member having an opening so disposed in relation to the said chambers that the shutter member is rotatable between a range of positions for each subsidiary chamber at which fluid flow is permitted through the shutter opening only between that subsidiary chamber and the main chamber, and through a range of positions in which the subsidiary chambers and main chamber are all mutually isolated.

2. An apparatus as claimed in claim 1, wherein there are two (first and second) subsidiary ports and respective subsidiary chambers.

3. An apparatus as claimed in claim 2, wherein the shutter member comprises a plate, the shutter opening being an aperture therein.

4. An apparatus as claimed in claim 2, wherein the first and second subsidiary chambers are spaced bores in a body portion of the valve, whose respective ends lie in said common plane sealing against the disc.

5. An apparatus as claimed in claim 2, wherein the minimum cross-section of the first subsidiary chamber is substantially larger than that of the second subsidiary chamber.

6. An apparatus as claimed in claim 3, wherein the plate is a disc, the aperture being off-set from the centre of the disc, and the shutter member further comprises a spindle connected to the disc for controlled rotation of the aperture about an axis.

7. An apparatus as claimed in claim 1, further comprising at least one accumulator reservoir connected between one of said first and second subsidiary ports and its respective source of gas pressure.

8. An apparatus as claimed in claim 1, including a pressure sensor for sensing gas pressure at or adjacent said main port or in said ventilator enclosure.

9. An apparatus as claimed in claim 1, which includes electronic circuitry for controlling said stepper motor to produce movement of said shutter member to provide a desired pattern of pressure changes at or adjacent said main port or in said ventilator.

* * * * *